(12) United States Patent
Ladant et al.

(10) Patent No.: US 6,333,154 B1
(45) Date of Patent: Dec. 25, 2001

(54) BACTERIAL MULTI-HYBRID SYSTEM AND APPLICATIONS THEREOF

(75) Inventors: Daniel Ladant, Cachan; Gouzel Karimova; Agnes Ullmann, both of Paris, all of (FR)

(73) Assignee: Institut Pasteur (FR)

( * ) Notice: Subject to any disclaimer, the term of this patent is extended or adjusted under 35 U.S.C. 154(b) by 0 days.

(21) Appl. No.: 09/203,681

(22) Filed: Dec. 1, 1998

Related U.S. Application Data

(60) Provisional application No. 60/067,308, filed on Dec. 4, 1997.

(51) Int. Cl.$^7$ ............................................. C12Q 1/68
(52) U.S. Cl. ................ 435/6; 435/7.32; 435/29; 435/488; 435/7.6; 530/350
(58) Field of Search ............................ 435/7.1, 7.2, 7.32, 435/7.6, 7.91, 29, 440, 488, 69.1, 4, 6; 530/350; 436/63, 808

(56) References Cited

U.S. PATENT DOCUMENTS 5,468,614 * 11/1995 Fields et al. ............................. 435/6
6,051,381    4/2000 Kornacker .

FOREIGN PATENT DOCUMENTS

PCT/US96/
   09809    6/1996  (WO) .

OTHER PUBLICATIONS

Ladant et al. (Journal of Biological Chemistry, vol. 264, No. 7, pp. 4015–4020), 1989.*

* cited by examiner

*Primary Examiner*—Donna C. Wortman
*Assistant Examiner*—Robert A. Zeman
(74) *Attorney, Agent, or Firm*—Finnegan, Henderson, Farabow, Garrett & Dunner, L.L.P.

(57) ABSTRACT

A signal amplification system comprises a bacterial multi-hybrid system, and more preferably a two-hybrid system, of at least two chimeric polypeptides containing a first chimeric polypeptide corresponding to a first fragment of an enzyme and a second chimeric polypeptide corresponding to a second fragment of an enzyme or a modulating substance capable of activating said enzyme. The first fragment is fused to a molecule of interest and the second fragment or the modulating substance is fused to a target ligand. The activity of the enzyme is restored by the in vivo interaction between the molecule of interest and the target ligand. Signal amplification is generated and, for example, triggers transcriptional activation. The signal amplification system is useful in a method of selecting a molecule of interest, which is capable of binding to target ligand, wherein the interaction between the molecule of interest and the target ligand is detected with the signal amplification system as a kit therefor. A method of screening for a substance capable of stimulating or inhibiting the interaction between a target ligand and a molecule of interest is also provided.

21 Claims, 7 Drawing Sheets

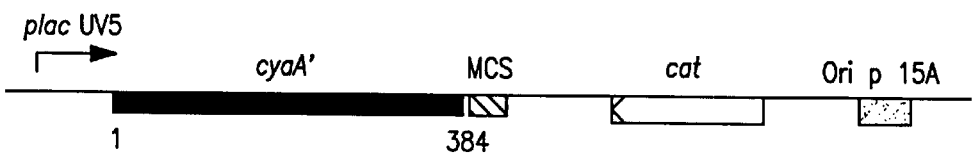
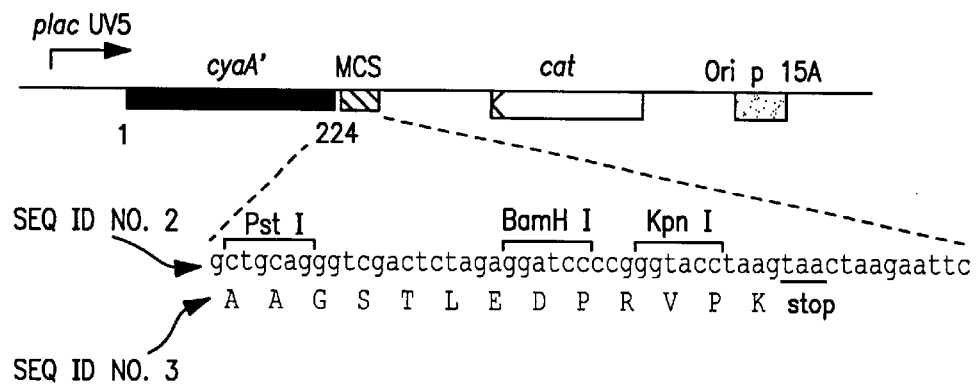
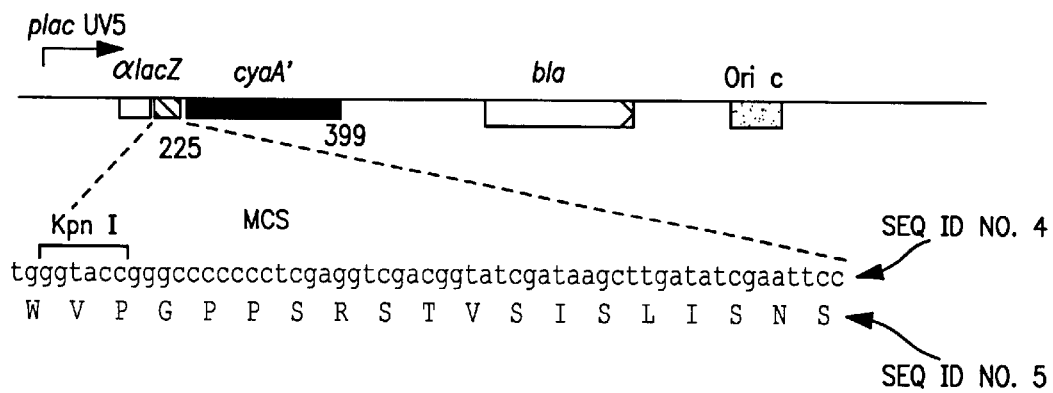
FIG. 2

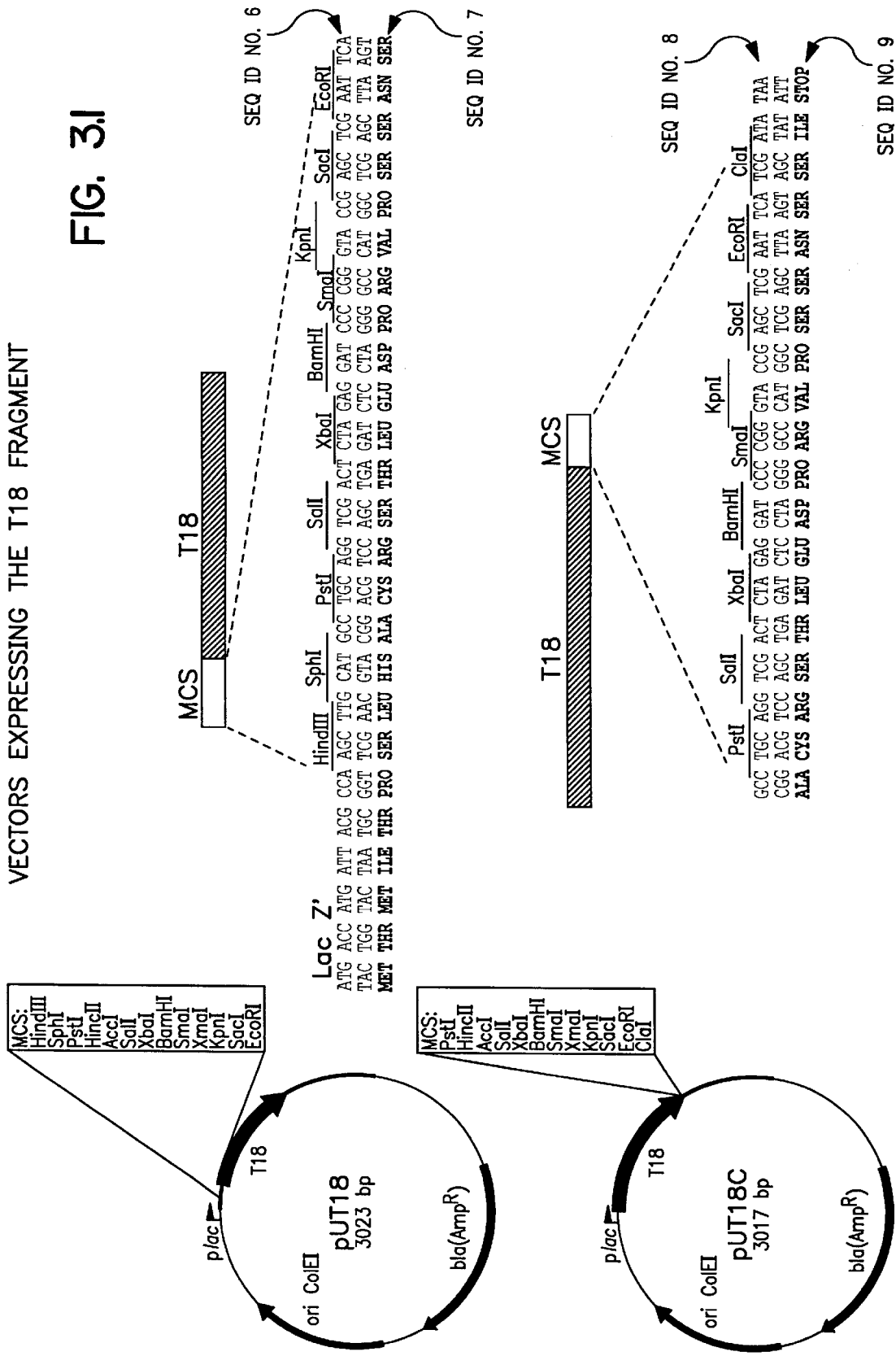
FIG. 3.1

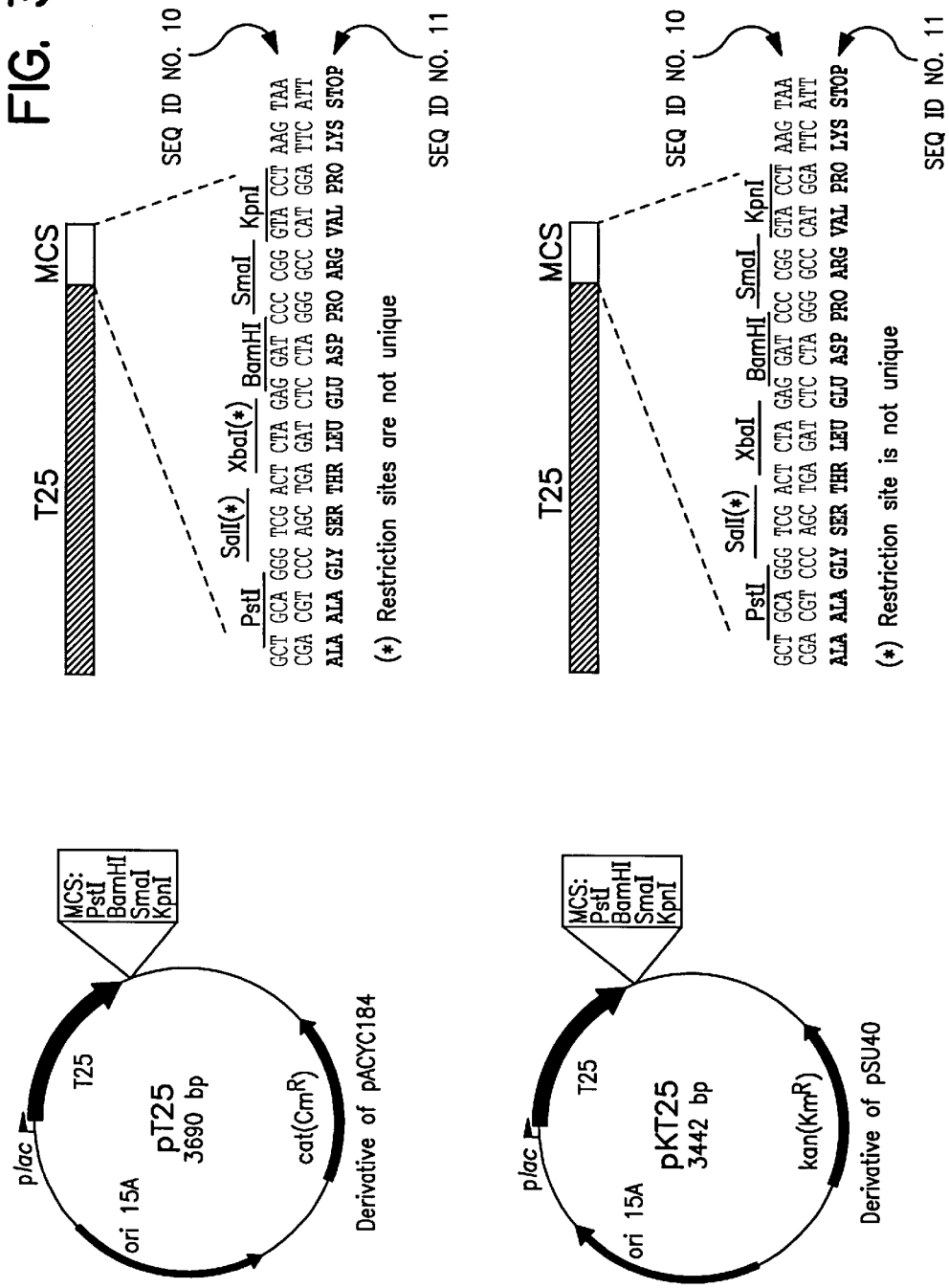
FIG. 3.2 VECTORS EXPRESSING THE T25 FRAGMENT

FIG. 5

SEQUENCE LISTING

<160> NUMBER OF SEQ ID NOS: 11

<210> SEQ ID NO 1
<211> LENGTH: 23
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 1
aattcatcga tataactaag taa                                              23

<210> SEQ ID NO 2
<211> LENGTH: 52
<212> TYPE: DNA
<213> ORGANISM: Artificial Sequence
<220> FEATURE:
<223> OTHER INFORMATION: Description of Artificial Sequence: Synthetic
      DNA
<221> NAME/KEY: CDS
<222> LOCATION: (1)..(39)

<400> SEQUENCE: 2 gct gca ggg tcg act cta gag gat ccc cgg gta cct aag taactaagaa        49
Ala Ala Gly Ser Thr Leu Glu Asp Pro Arg Val Pro Lys
 1               5                  10 ttc                                                                   52

<210> SEQ ID NO 3
<211> LENGTH: 13
<212> TYPE: PRT
<213> ORGANISM: Artificial Sequence
<220> FEATURE:
<223> OTHER INFORMATION: Description of Artificial Sequence: Synthetic
      amino acid

<400> SEQUENCE: 3

Ala Ala Gly Ser Thr Leu Glu Asp Pro Arg Val Pro Lys
 1               5                  10

<210> SEQ ID NO 4
<211> LENGTH: 57
<212> TYPE: DNA
<213> ORGANISM: Artificial Sequence
<220> FEATURE:
<223> OTHER INFORMATION: Description of Artificial Sequence: Synthetic
      DNA
<221> NAME/KEY: CDS
<222> LOCATION: (1)..(57)

<400> SEQUENCE: 4 tgg gta ccg ggc ccc ccc tcg agg tcg acg gta tcg ata agc ttg ata       48
Trp Val Pro Gly Pro Pro Ser Arg Ser Thr Val Ser Ile Ser Leu Ile
 1               5                  10                  15 tcg aat tcc                                                           57
Ser Asn Ser <210> SEQ ID NO 5
<211> LENGTH: 19
<212> TYPE: PRT
<213> ORGANISM: Artificial Sequence
<220> FEATURE:
<223> OTHER INFORMATION: Description of Artificial Sequence: Synthetic
      amino acid

```
<400> SEQUENCE: 5

Trp Val Pro Gly Pro Pro Ser Arg Ser Thr Val Ser Ile Ser Leu Ile
 1               5                  10                  15

Ser Asn Ser

<210> SEQ ID NO 6
<211> LENGTH: 75
<212> TYPE: DNA
<213> ORGANISM: Artificial Sequence
<220> FEATURE:
<223> OTHER INFORMATION: Description of Artificial Sequence: Synthetic
      DNA
<221> NAME/KEY: CDS
<222> LOCATION: (1)..(75)

<400> SEQUENCE: 6 atg acc atg att acg cca agc ttg cat gcc tgc agg tcg act cta gag      48
Met Thr Met Ile Thr Pro Ser Leu His Ala Cys Arg Ser Thr Leu Glu
 1               5                  10                  15 gat ccc cgg gta ccg agc tcg aat tca                                   75
Asp Pro Arg Val Pro Ser Ser Asn Ser
                20                  25

<210> SEQ ID NO 7
<211> LENGTH: 25
<212> TYPE: PRT
<213> ORGANISM: Artificial Sequence
<220> FEATURE:
<223> OTHER INFORMATION: Description of Artificial Sequence: Synthetic
      amino acid

<400> SEQUENCE: 7

Met Thr Met Ile Thr Pro Ser Leu His Ala Cys Arg Ser Thr Leu Glu
 1               5                  10                  15

Asp Pro Arg Val Pro Ser Ser Asn Ser
                20                  25

<210> SEQ ID NO 8
<211> LENGTH: 57
<212> TYPE: DNA
<213> ORGANISM: Artificial Sequence
<220> FEATURE:
<223> OTHER INFORMATION: Description of Artificial Sequence: Synthetic
      DNA
<221> NAME/KEY: CDS
<222> LOCATION: (1)..(54)

<400> SEQUENCE: 8 gcc tgc agg tcg act cta gag gat ccc cgg gta ccg agc tcg aat tca      48
Ala Cys Arg Ser Thr Leu Glu Asp Pro Arg Val Pro Ser Ser Asn Ser
 1               5                  10                  15 tgc ata taa                                                           57
Cys Ile <210> SEQ ID NO 9
<211> LENGTH: 18
<212> TYPE: PRT
<213> ORGANISM: Artificial Sequence
<220> FEATURE:
<223> OTHER INFORMATION: Description of Artificial Sequence: Synthetic
      amino acid

<400> SEQUENCE: 9

Ala Cys Arg Ser Thr Leu Glu Asp Pro Arg Val Pro Ser Ser Asn Ser
 1               5                  10                  15
```

-continued

```
Cys Ile

<210> SEQ ID NO 10
<211> LENGTH: 42
<212> TYPE: DNA
<213> ORGANISM: Artificial Sequence
<220> FEATURE:
<223> OTHER INFORMATION: Description of Artificial Sequence: Synthetic
      DNA
<221> NAME/KEY: CDS
<222> LOCATION: (1)..(39)

<400> SEQUENCE: 10 gct gca ggg tcg act cta gag gat ccc cgg gta cct aag taa           42
Ala Ala Gly Ser Thr Leu Glu Asp Pro Arg Val Pro Lys
  1               5                  10

<210> SEQ ID NO 11
<211> LENGTH: 13
<212> TYPE: PRT
<213> ORGANISM: Artificial Sequence
<220> FEATURE:
<223> OTHER INFORMATION: Description of Artificial Sequence: Synthetic
      amino acid

<400> SEQUENCE: 11

Ala Ala Gly Ser Thr Leu Glu Asp Pro Arg Val Pro Lys
  1               5                  10
```

BACTERIAL MULTI-HYBRID SYSTEM AND APPLICATIONS THEREOF

CROSS-REFERENCE TO RELATED APPLICATION

This regular U.S. application is based on and claims the benefit of U.S. Provisional patent application Ser. No. 60/067,308, filed Dec. 4, 1997, the entire disclosure of which is relied upon and incorporated by reference herein.

BACKGROUND OF THE INVENTION

The present invention concerns a method for selecting a molecule, and kit thereof, a method for screening a molecule, and kit thereof, and a signal amplification system comprising a bacterial multi-hybrid system.

The present invention relates to a signal amplification system comprising a bacterial multi-hybrid system, and more preferably a two-hybrid system, of at least two chimeric polypeptides containing a first chimeric polypeptide corresponding to a first fragment of an enzyme and a second chimeric polypeptide corresponding to a second fragment of an enzyme or a modulating substance capable of activating said enzyme, wherein the first fragment is fused to a molecule of interest and the second fragment or the modulating substance is fused to a target ligand, and wherein the activity of the enzyme is restored by the interaction between the said molecule of interest and the said target ligand, and wherein a signal amplification is generated.

The present invention also relates to a method of selecting a molecule of interest, which is capable of binding to a target ligand, wherein the interaction between the said molecule of interest and the said target ligand is detected with a signal amplification system according to the invention, by means of generating a signal amplification and triggering transcriptional activation.

The present invention also relates to a method of screening for a substance capable of stimulating or inhibiting the interaction between a target ligand and a molecule of interest, wherein respectively the stimulating or the inhibiting activity is detected with a signal amplification system according to the invention, by means of generating a signal amplification and respectively of triggering or of abolishing transcriptional activation, and wherein said signal amplification and said triggered or abolished transcriptional activation are compared with those obtained from an identical signal amplification system without any substance.

Most biological processes involve specific protein-protein interactions. General methodologies to identify interacting proteins or to study these interactions have been extensively developed. Among them, the yeast two-hybrid system currently represents the most powerful in vivo approach to screen for polypeptides that could bind to a given target protein. Originally developed by Fields and coworkers [Fields, S. & Song, O. (1989) Nature 340, 245–6; Chien, C. T., Bartel, P. L., Sternglanz, R. & Fields, S. (1991) Proc. Natl. Acad. Sci. USA. 88, 9578–82. Two American U.S. Pat. No. 5,283,173 granted on Feb. 1, 1994 (Fields, S. & Song, O.) and U.S. Pat. No. 5,468,614 granted on Nov. 21, 1995 (Fields, S. & Song, O.) are also incorporated by reference], it utilizes hybrid genes to detect protein-protein interactions by means of direct activation of a reporter-gene expression (Allen, J. B., Walberg, M. W., Edwards, M. C. & Elledge, S. J. (1995) Trends Biochem. Sci. 20, 511–6; Transy, C. & Legrain, P. (1995) Mol. Biol. Rep. 21, 119–27).

In essence, the two putative protein partners are genetically fused to the DNA-binding domain of a transcription factor and to a transcriptional activation domain, respectively. A productive interaction between the two proteins of interest will bring the transcriptional activation domain in the proximity of the DNA-binding domain and will trigger directly the transcription of an adjacent reporter gene (usually lacZ or a nutritional marker) giving a screenable phenotype. As there is evidence that the transcription can be activated through the use of two functional domains of a transcription factor: a domain that recognizes and binds to a specific site on the DNA and a domain that is necessary for activation, as reported by Keegan et al. (1986) Science 231, 699–407 and Ma and Ptashne (1987) Cell 48, 847–853.

Recently, Rossi et al. (Rossi, F., Charlton, C. A. & Blau, H. M. (1997) Proc. Natl. Acad. Sci. USA. 94, 8405–8410) described a different approach, a mammalian "two-hybrid" system, which uses β-galactosidase complementation (Ullmann, A., Jacob, F. & Monod, J. (1968) J. Mol. Biol. 32, 1–13) to monitor protein-protein interactions in intact eukaryotic cells.

Phage display (Smith, G. P. (1985) Science 228, 1315–7; Scott, J. K. & Smith, G. P. (1990) Science 249, 386–90) and double-tagging assay (Germino, F. J., Wang, Z. X. & Weissman, S. M. (1993) Proc. Natl. Acad. Sci. USA. 90, 933–7) represent alternative approaches to screen complex libraries of proteins for direct interaction with a given ligand. However, these techniques do not allow an in vivo selection of the relevant clones.

Another approach is described in the International Patent Application No. WO 96/40987 (Schatz, P. J. et al.), which provides random peptide libraries and methods for generating and screening libraries to identify peptides that bind to receptor molecules of interest, including antibodies. The peptide library is constructed so that the DNA binding protein-random peptide fusion product can bind to the recombinant DNA expression vector that encodes the fusion product that contains the peptide of interest. The method of generating the peptide library comprises the steps of (a) constructing a recombinant DNA vector that encodes a DNA binding protein and contains binding sites for the DNA binding protein; (b) inserting into the coding sequence of the DNA binding protein in a multiplicity of vectors of step (a) coding sequences for random peptides such that the resulting vectors encode different fusion proteins, each of which is composed of the DNA binding protein and a random peptide; (c) transforming host cells with the vectors of steps (b); and (d) culturing the host cells transformed in step (c) under conditions suitable for expression of the fusion proteins. Typically, a random peptide library will contain at least $10^6$ to $10^8$ different members, although library sizes of $10^8$ to $10^{13}$ can be achieved.

A novel variety of approach is defined in the International Patent Application No. WO 96/29429 (Wickens, M. & Fields, S.) related to a hybrid system to detect protein-RNA interactions using the same method of achievement as recited in the two above-mentioned American patents. This hybrid system has a first hybrid protein comprising a DNA-binding domain and a first RNA-binding domain, a second hybrid protein comprising a transcriptional activation domain and a second RNA-binding domain, and a hybrid RNA. The interaction between both the first RNA-binding domain and the hybrid RNA and the second RNA-binding domain and the hybrid RNA causes the transcriptional activation domain to activate transcription of the detectable gene.

Bartel, P. L., Roecklein, J. A., SenGupta, D. & Fields, S. (1996) Nat. Genet. 12, 72–77 extended the approach of the typical two-hybrid system consisting in a known protein that forms a part of a DNA-binding domain hybrid, assayed against a library of all possible proteins present as transcriptional activation domain hybrids, using the genome of the bacteriophage T7, such that a second library of all possible proteins is fused to the DNA-binding domain to be analyzed. This genome-wide approach to the two-hybrid searches has identified 25 interactions among the proteins of T7.

SUMMARY OF THE INVENTION

The aim of the present invention is to provide a novel bacterial multi-hybrid system, and more preferably a two-hybrid system, in which proteins of interest are genetically fused to two complementary fragments of a catalytic domain of an enzyme, which provides significant advantages over the prior art.

Thus, the present invention provides a signal amplification system comprising a bacterial multi-hybrid system, and more preferably a two-hybrid system, of at least two chimeric polypeptides containing a first chimeric polypeptide corresponding to a first fragment of an enzyme and a second chimeric polypeptide corresponding to a second fragment of an enzyme or a modulating substance capable of activating said enzyme, wherein the first fragment is fused to a molecule of interest and the second fragment or the modulating substance is fused to a target ligand, and wherein the activity of the enzyme is restored by the interaction between the said molecule of interest and the said target ligand, and wherein a signal amplification is generated.

This system allows an easy in vivo screening and selection of functional interactions between the target ligand and the molecule of interest.

A genetic test is based on the reconstitution, in a specific enzyme deficient bacteria, of a signal transduction pathway that takes advantage of the positive control exerted by a signaling molecule. Association of the target ligand and the molecule of interest results in functional complementation between the two chimeric polypeptides and leads to the signaling molecule synthesis. The signaling molecule then triggers transcriptional activation of catabolic operons, of a gene conferring resistance to antibiotics, of a gene encoding for a toxin or of a color marker, such as a fluorescent marker of the type of the Green Fluorescent Protein (GFP) that yields a characteristic phenotype. In this genetic test of screening and/or selection, the involvement of a signaling cascade offers the unique property that association between the chimeric polypeptides can be spatially separated from the transcriptional activation readout. This permits a versatile design of screening procedures either for ligands that bind to a given "bait", as in the classical yeast multi-hybrid system, or for molecules or mutations that block a given interaction between two proteins of interest.

Furthermore, because the signal amplification system according to the invention involves the generation of at least one signaling molecule, also called regulatory molecule, the physical association of the two putative interacting target ligand and molecule of interest can be spatially separated from the transcriptional events that are dependent on regulatory molecule synthesis. This means that the interaction between a target ligand and a molecule of interest under study does not need to take place in the vicinity of the transcription machinery as is the case for the yeast two-hybrid system as described above. Hence, in addition to the methods described above, the present invention allows one to analyze more particularly protein interactions that occur either in the cytosol or at the inner membrane level.

Another advantage of the present invention over the prior art is that this bacterial system is particularly versatile as it offers the possibility of both positive and negative selections. Positive selection means bacterial growth, for example, on minimal medium containing lactose or maltose. Negative selection means arrest of growth.

The present invention further relates to a method of selecting a molecule of interest, which is capable of binding to a target ligand, wherein the interaction between the said molecule of interest and the said target ligand is detected with a signal amplification system according to the invention, by means of generating a signal amplification and triggering transcriptional activation.

The present invention also relates to a method of screening for a substance capable of stimulating or inhibiting the interaction between a target ligand and a molecule of interest, wherein the stimulating or the inhibiting activity is detected with a signal amplification system according to the invention, by means of generating a signal amplification and triggering transcriptional activation, and wherein said signal amplification and said triggering transcriptional activation are compared with those obtained from an identical signal amplification system without any substance.

The present invention also provides a kit for selecting a molecule of interest, wherein said kit comprises:

(a) a signal amplification system according to the invention;

(b) an *E. coli* strain, or a bacterial strain, or an eukaryotic cell deficient in endogenous adenylate cyclase; and (c) a medium allowing the detection of the complementation selected from the group consisting of indicator or selective medium, for example, as minimal medium supplemented with lactose or maltose as unique carbon source, medium with antibiotics, medium to visualize fluorescence, conventional medium, and medium that allows the sorting by the presence of the phage receptor.

Further, the present invention also provides a kit for selecting a molecule of interest, wherein said kit comprises:

(a) a signal amplification system according to the invention, wherein the molecule of interest is a mutant molecule compared to the known wild type molecule;

(b) a signal amplification system according to the invention, wherein the molecule of interest is the known wild type molecule as the control;

(c) *E. coli* strain, or in any bacterial strain deficient in endogenous adenylate cyclase, or any other eukaryotic cell;

(d) a medium allowing the detection of the complementation selected from the group consisting of indicator plate or selective medium as minimal medium supplemented with lactose or maltose as unique carbon source medium with antibiotics, medium to visualize fluorescence, conventional medium, and medium that allows the sorting by the presence of the phage receptor for each signal amplification system; and (e) means for detecting whether the signal amplification system with the mutant molecule is enhanced or inhibited with respect to the signal amplification system with the wild type molecule.

The present invention also provides a kit for screening for a substance capable of stimulating or inhibiting the interaction between a target ligand and a molecule of interest, wherein said kit comprises:

(a) a signal amplification system according to the invention with the substance capable of stimulating or inhibiting the interaction between a target ligand and a molecule of interest;

(b) a signal amplification system according to the invention without any substance as the control;

(c) *E. coli* strain, or in any bacterial strain deficient in endogenous adenylate cyclase, or any other eukaryotic cell and;

(d) a medium allowing the detection of the complementation selected from the group consisting of indicator plate or selective medium as minimal medium supplemented with lactose or maltose as unique carbon source, medium with antibiotics, medium to visualize fluorescence, conventional medium, and medium which allows the sorting by the presence of the phage receptor;

(e) means for detecting whether the signal amplification system with the substance is enhanced or inhibited with respect to the signal amplification system without any substance.

According to one embodiment of the present invention, the signal amplification system comprises a bacterial multi-hybrid system, and more preferably a two-hybrid system, containing a first chimeric polypeptide corresponding to a first fragment of an enzyme, a second chimeric polypeptide corresponding to a second fragment of an enzyme or a modulating substance capable of activating said enzyme, and a substance capable of stimulating or inhibiting the interaction between a target ligand and a molecule of interest.

The present invention also provides a method of screening for a substance capable of stimulating or inhibiting the interaction between a target ligand and a molecule of interest, wherein the stimulating or the inhibiting activity is detected with a signal amplification system according to the invention, by means of generating a signal amplification and triggering transcriptional activation, and wherein said signal amplification and said triggering transcriptional activation are compared with those obtained from an identical signal amplification system without any substance.

BRIEF DESCRIPTION OF THE DRAWINGS

This invention will be described in greater detail with reference to the drawings in which.

The upper part schematizes the basic principle of in vivo complementation between the two fragments of the catalytic domain of *B. pertussis* adenylate cyclase. The two boxes represent the T25 and T18 fragments corresponding to amino acids 1 to 224 and 225 to 399 of the CyaA protein. In A, the full-length catalytic domain (residues 1 to 399), when expressed in *E.coli*, exhibits a basal calmodulin-independent activity that results in cyclic adenosine monophosphate (cAMP) synthesis. In B, the two fragments T25 and T18, when coexpressed as independent polypeptides, are unable to interact and no cAMP synthesis occurs. In C, the two fragments, fused to two interacting proteins, X and Y, are brought into close proximity resulting in functional complementation, followed by cAMP production.

The lower part schematizes the readout of the complementation. cAMP, synthesized in an *E. coli* cya strain by the complementing T25 and T18 pairs, binds to the catabolite activator protein, CAP. The cAMP/CAP complex (C) can then recognize specific promoters and switch on the transcription of the corresponding genes. These reporter genes can be either natural *E.coli* genes, such as lacZ or mal genes, or synthetic ones, such as antibiotic resistance genes fused to a cAMP/CAP dependent promoter.

FIG. 2 is a schematic representation of plasmids.

The open boxes represent the open reading frames of β-lactamase (bla) and chloramphenicol acetyl transferase (cat) genes. The dark boxes correspond to the open reading frame of cyaA' with codon numbers indicated below. The hatched boxes correspond to the multicloning site sequences (MCS) that are fused at the indicated position of the cya open reading frame. The origin of replication of the plasmids is indicated by dotted boxes.

FIG. 3.1 and FIG. 3.2 are schematic representations of other plasmids.

The left part represents the maps of the plasmids, with the different antibiotic-selectable markers (chloramphenicol acetyl transferase (cat), aminoglycoside phosphotransferse (kan) and β-lactamase (bla), the origin of replication and the position of the multicloning site sequences (MCS) relative to the T25 and T18 open reading frames. The right part describes the nucleotide sequence of the multicloning site sequences (MCS) fused to T25 (FIG. 3.2) or T18 (FIG. 3.1) and the corresponding reading frames.

Figure 4B:
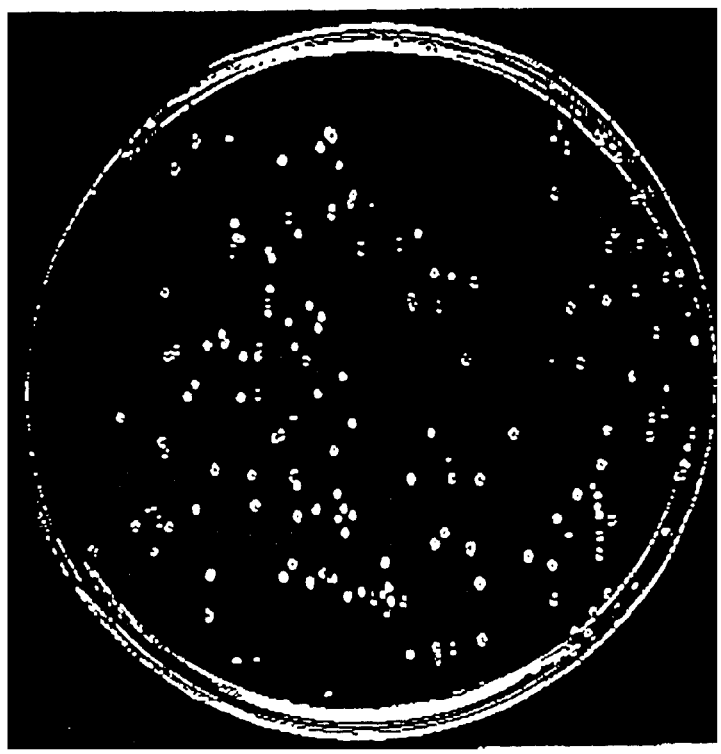
Figure 4A:
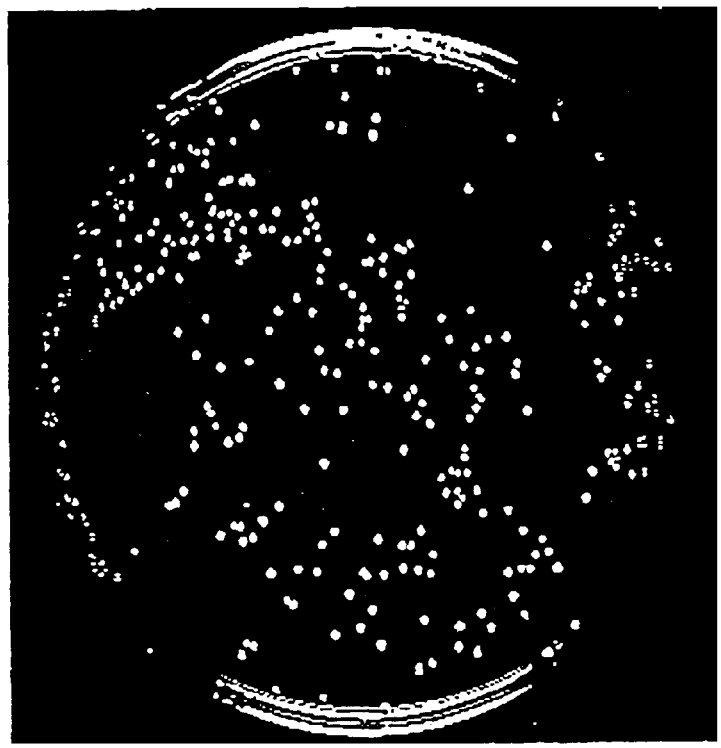

FIG. 4 depicts the results of screening of interacting proteins with the bacterial two-hybrid system.

DHPI cells were cotransformed with a mixture of plasmids pT18, pT18-zip, and PT18-Tyr, and either pT25 (A) or pT25-zip (B), plated on LB-X-Gal agar plates containing 0.5 mM IPTG, ampicillin and chloramphenicol, and incubated for 30 hrs at 30° C. Note that the cya$^+$ colonies are larger than the cya ones.

Figure 5:
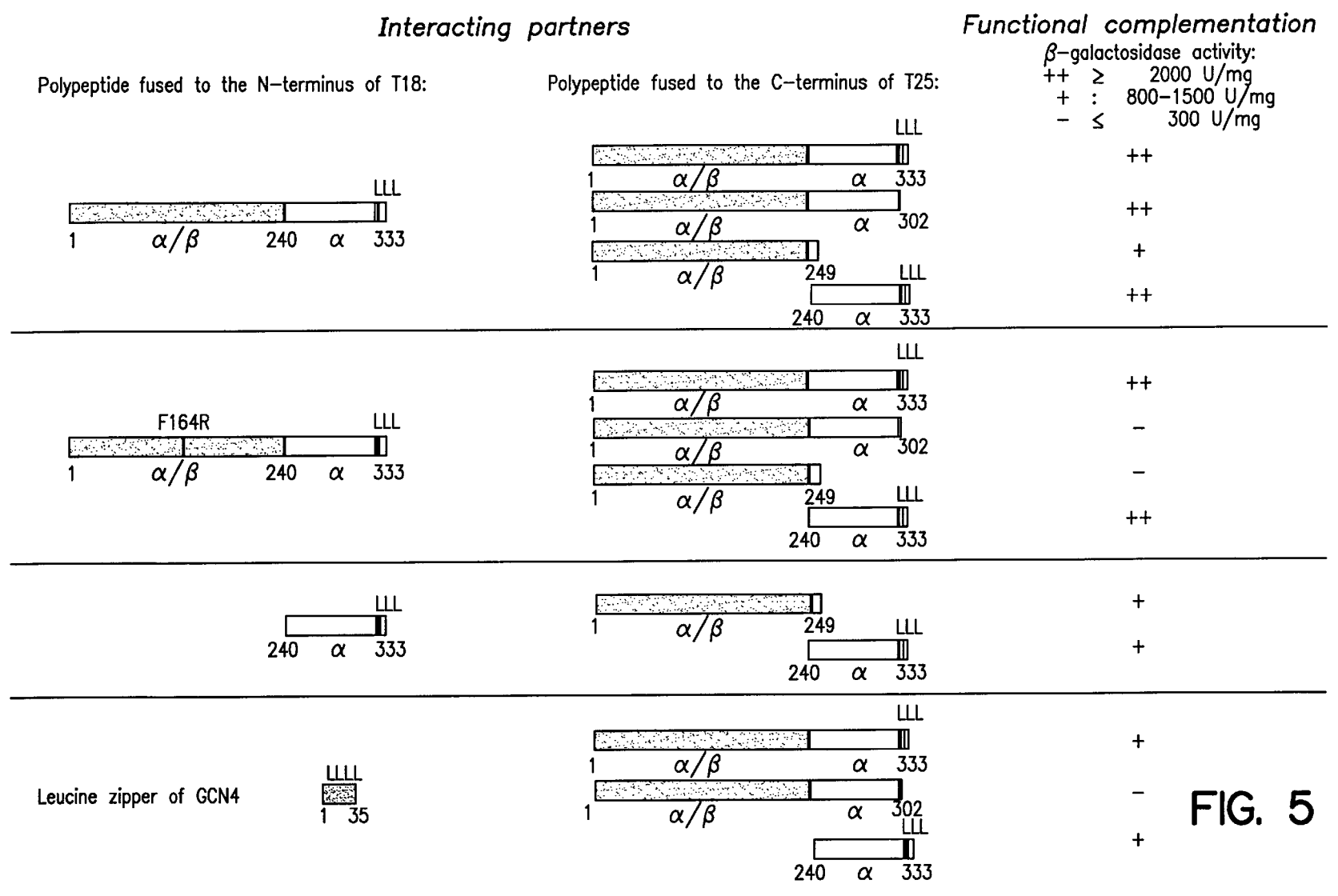

FIG. 5 relates to the mapping of interacting domains of the *B. stearothermophilus* tyrosyl-tRNA synthetase.

DNA fragments encoding the indicated polypeptide segments of the tyrosyl-tRNA synthetase (the numbers correspond to the amino acid residues) were amplified by PCR using appropriate primers and cloned into pT25 and/or pT18. The functional complementation between the indicated chimeric proteins was assayed on DHP1 cells co-transformed with the corresponding plasmids by measuring the β-galactosidase activity.

Figure 6:
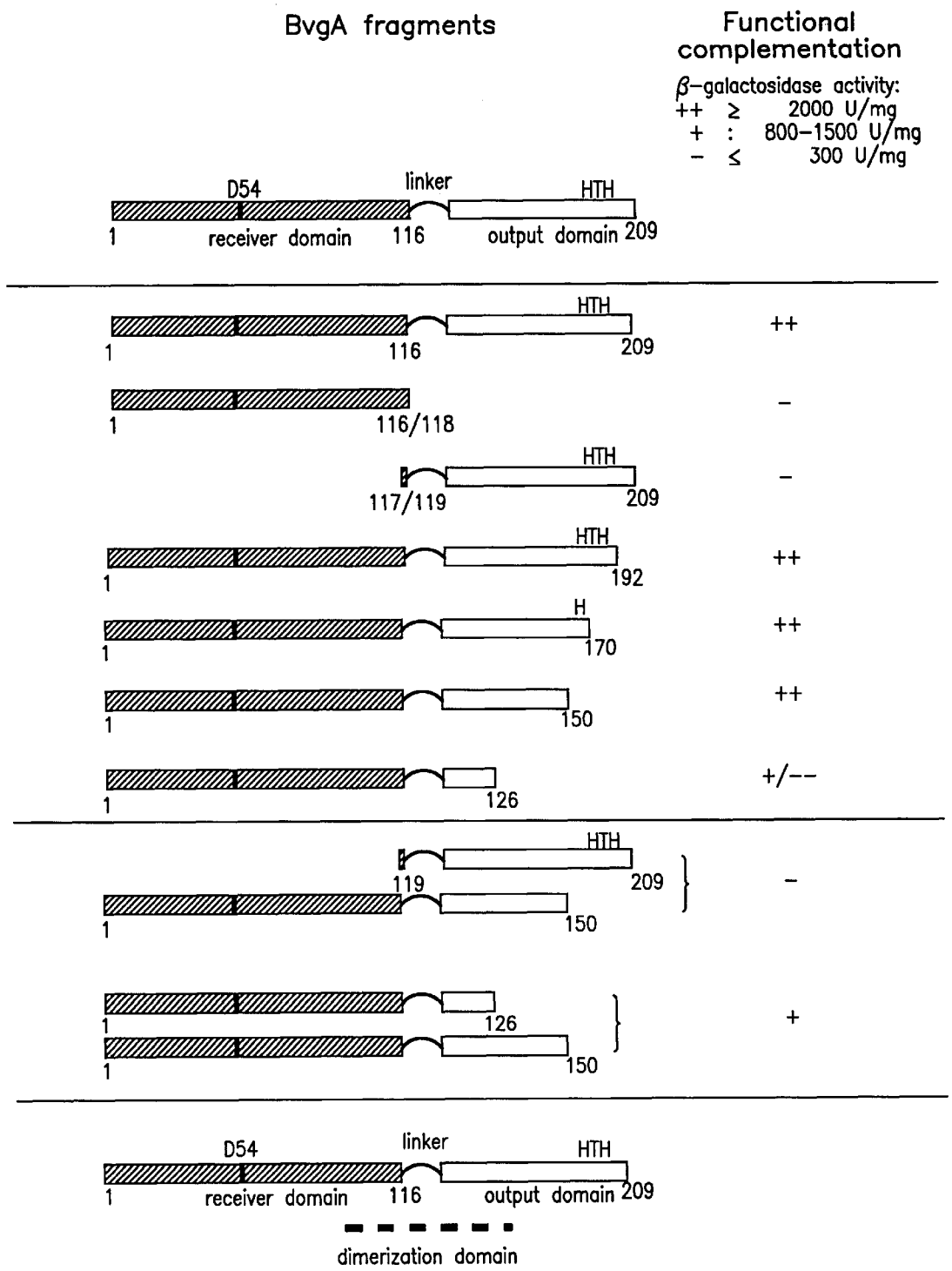

FIG. 6 relates to the mapping of interacting domains of *B. pertussis* B.vgA.

DNA fragments encoding indicated polypeptide segments of BvgA (the numbers correspond to the amino acid residues) were amplified by PCR using appropriate primers and cloned into pKT25 and/or pUTT18C. The functional complementation between the indicated chimeric proteins was assayed on DHP1 cells co-transformed with the corresponding plasmids by measuring the β-galactosidase activity.

DETAILED DESCRIPTION OF THE INVENTION

Thus, the present invention provides a novel signal amplification system in *Escherichia coli*, in which the proteins of interest are genetically fused to two complementary fragments of the catalytic domain of *Bordetella pertussis* adenylate cyclase (Ladant, D. (1988) *J. Biol. Chem.* 263, 2612–2618; Ladant, D., Michelson, S., Sarfati, R. S., Gilles, A.-M., Predeleanu, R. & Blrzu, O. (1989) *J. Biol. Chem.* 264, 4015–4020).

*B. pertussis* produces a calmodulin dependent adenylate cyclase toxin encoded by the cyaA gene (Hewlett, E. L., Urban, M. A., Manclark, C. R. & Wolff, J. (1976) *Proc. Natl.*

Acad. Sci. U.S.A. 73, 1926–1930; Glaser, P., Ladant, D., Sezer, O., Pichot, F., Ullmann, A. & Danchin, A. (1988) *Mol. Microbiol.* 2, 19–30; Mock, M. & Ullmann, A. (1993) *Trends Microbiol.* 1, 187–192). The catalytic domain is located within the first 400 amino acids of this 1706 residue-long protein (Ladant, D., Michelson, S., Sarfati, R. S., Gilles, A.-M., Predeleanu, R. & Blrzu, O. (1989) *J. Biol. Chem.* 264, 4015–4020; Glaser, P., Ladant, D., Sezer, O., Pichot, F., Ullmann, A. & Danchin, A. (1988) *Mol. Microbiol.* 2, 19–30). It exhibits a high catalytic activity (kcat= 2000 s-1) in the presence of calmodulin (CaM), and a low but detectable activity (kcat=2 s-1) in the absence of this activator (Ladant, D. (1988) *J. Biol. Chem.* 263, 2612–2618; Wolff, J., Cook, G. H., Goldhammer, A. R. & Berkowitz, S. A. (1980) *Proc. Natl. Acad. Sci. USA.* 77, 3841–3844).

Biochemical studies revealed that the catalytic domain can be proteolytically cleaved into two complementary fragments, T25 and T18, that remain associated in the presence of CaM in a fully active ternary complex (Ladant, D. (1988) *J. Biol. Chem.* 263, 2612–2618; Ladant, D., Michelson, S., Sarfati, R. S., Gilles, A.-M., Predeleanu, R. & Blrzu, O. (1989) *J. Biol. Chem.* 264, 4015–4020; Munier, H., Gilles, A. M., Glaser, P., Krin, E., Danchin, A., Sarfati, R. & Barzu, O. (1991) *Eur. J. Biochem.* 196, 469–74). In the absence of CaM, the mixture of the two fragments did not exhibit detectable activity suggesting that the two fragments are not able to reassociate to yield basal CaM-independent activity.

The two complementary fragments, T25 and T18, that are both necessary to form an active enzyme, in the presence of CaM when expressed in *E. coli* as separated entities, are unable to recognize each other and cannot reconstitute a functional enzyme. However, when T25 and T18 are fused to peptides or proteins that are able to interact, heterodimerization of these chimeric polypeptides results in a functional complementation between the adenylate cyclase fragments.

Figure 1:
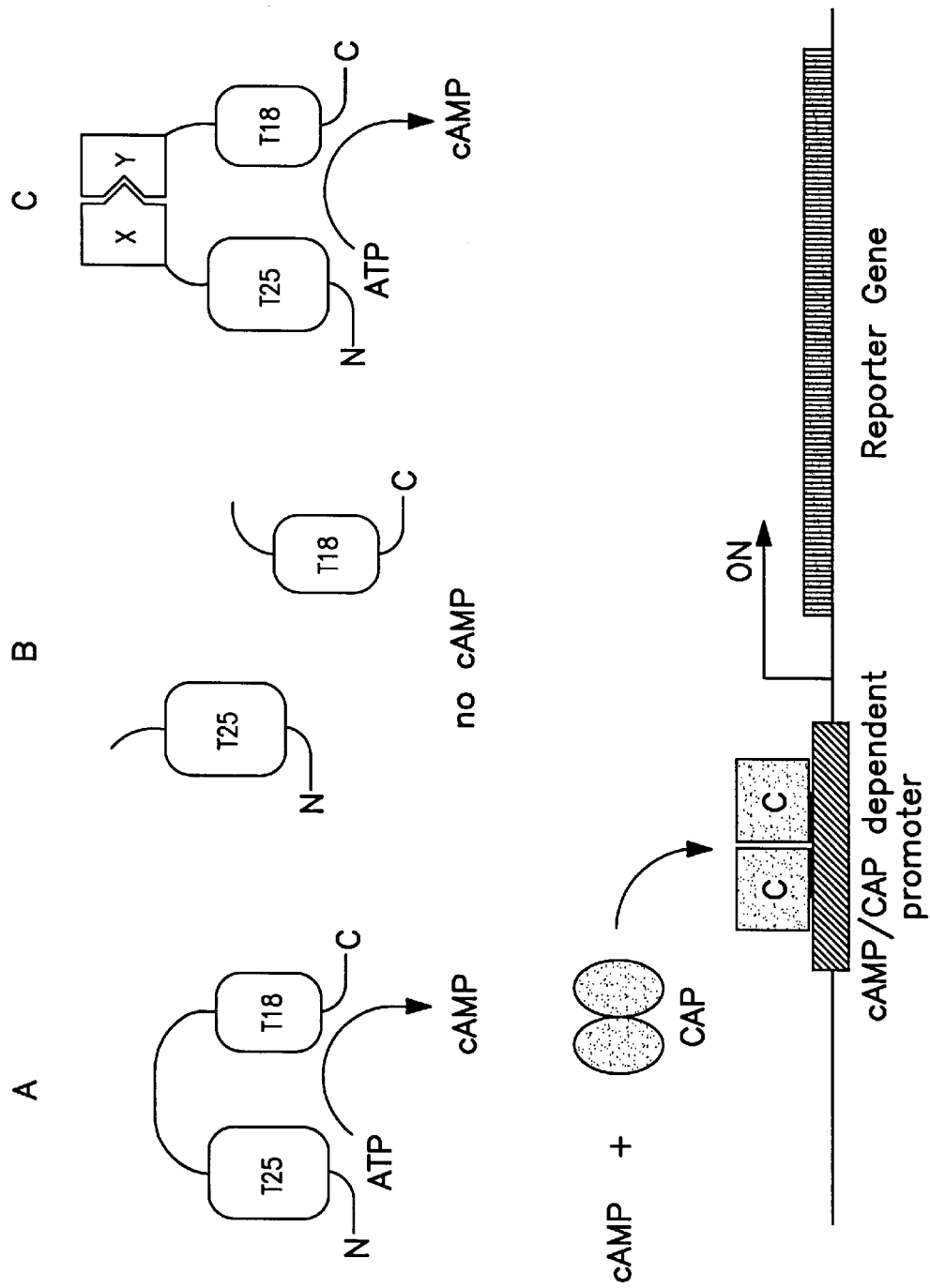
FIG. 1 depicts the principle of an *E. coli* multi-hybrid system based on functional complementation of the catalytic domain of Bordetella adenylate cyclase (CyaA) fragments.

When expressed in an adenylate cyclase deficient *E. coli* strain (*E. coli* lacks CaM or CaM-related proteins), the T25 and T18 fragments fused to putative interacting proteins reassociate and lead to cAMP synthesis (FIG. 1).

Interaction between a target ligand and a molecule of interest results in functional complementation between the two adenylate cyclase fragments leading to cAMP synthesis, which in turn can trigger the expression of several resident genes. Using this assay, one can select specific clones expressing a protein that interacts with a given target by a simple genetic screening.

The present invention provides a signal amplification system comprising a bacterial multi-hybrid system, and more preferably a two-hybrid system, of at least two chimeric polypeptides containing a first chimeric polypeptide corresponding to a first fragment of an enzyme, and a second chimeric polypeptide corresponding to a second fragment of an enzyme or a modulating substance capable of activating said enzyme, wherein the first fragment is fused to a molecule of interest and the second fragment or the modulating substance is fused to a target ligand, and wherein the activity of the enzyme is restored by the interaction between the said molecule of interest and the said target ligand, and wherein a signal amplification is generated.

"Signal amplification system" means a system involving the interaction between at least two chimeric polypeptides leading to the production of a large number of signaling molecules.

"Signal amplification" means, in the present invention, that the number of signaling molecules is higher than the number of chimeric polypeptides that produced it.

The first fragment and the second fragment are issued from the same enzyme or not. In any case, the first and the second fragments are distinct from each other even if they are issued from the same enzyme. For example, the fragments are from residues 1 to 224 and 225 to 399 from *B. Pertussis* adenylate cyclase.

A fragment issued from the enzyme comprises between 20 and 400 amino acid residues and more preferably 200 consecutive amino acid residues.

"Modulating substance" refers to a substance capable of activating or inhibiting an enzyme, which is an activator, natural or not, of the enzyme a fragment thereof, or a derivative of the activator; the enzyme having a modulating substance-binding site. In a preferred embodiment of the invention, the modulating substance is a natural activator as, for example, the calmodulin.

The fragments and the modulating substance are fused, respectively, to the molecule of interest or to the target ligand by means of genetic recombination as described herein after. A proteolytic cleavage site can be introduced, according to the well known techniques, in the genetic construction between a fragment of the enzyme and a molecule of interest in order to eliminate easily, after the generation of the signal amplification, by restriction enzyme the fragment and to recover the molecule of interest.

The molecule of interest can be detected for example from cDNA, genomic, or synthetic random DNA libraries.

The restoration of the enzymatic activity means that an enzyme activity is recovered.

The interaction between the molecule of interest and the target ligand means that there exists a recognition which could possibly lead to the binding between the molecule of interest and the target ligand.

According to the invention, the enzyme is selected from the group consisting of adenylate cyclase and guanylate cyclase from any origin. Any origin refers to Bordetella species or any other organism that produces this type of enzyme.

In one specific illustration of the present invention the enzyme is the catalytic domain of Bordetella adenylate cyclase (CyaA) located within the first 400 amino acid residues of the adenylate cyclase toxin.

The present invention also concerns a first fragment and a second fragment, which are any combination of fragments from the same enzyme, which in vitro functionally interact with the natural activator of said enzyme by restoring its activity.

According to one embodiment of the invention the first and the second fragments are selected from the group consisting of:

(a) a fragment T25 corresponding to amino acids 1 to 224 of CyaA and a fragment T18 corresponding to amino acids 225 to 399 of CyaA;

(b) a fragment corresponding to amino acids 1 to 224 of CyaA and a fragment corresponding to amino acids 224 to 384 of CyaA;

(c) a fragment corresponding to amino acids 1 to 137 of CyaA and a fragment corresponding to amino acids 138 to 400 of CyaA;

(d) a fragment corresponding to amino acids 1 to 317 of CyaA and a fragment corresponding to amino acids 318 to 400 of CyaA; and (e) two fragments from eukaryotic adenylate cyclase in association with molecules, such as, G protein and forskolin.

According to a preferred embodiment of the invention, the first and the second fragments are a fragment T25 corresponding to amino acids 1 to 224 of *Bordetella pertussis* CyaA and a fragment T18 corresponding to amino acids 225 to 399 of *Bordetella pertussis* CyaA.

According to the invention, the modulating substance is a natural activator, or a fragment thereof, of the enzyme. In a specific embodiment of the invention, the natural activator is the calmodulin (CaM), or a fragment thereof, and said first fragment is mutated compared to the wild type enzyme. The fragment of calmodulin is about 70 amino acids long, corresponding preferentially, to residues 77 to 148 of mammalian calmodulin.

According to another aspect, the invention also concerns a first fragment, which is a mutated fragment of the catalytic domain of Bordetella adenylate cyclase (CyaA). "Mutated fragment" means that it presents at least one mutation in the polynucleotide sequence, said fragment in combination with a second fragment can then in vivo functionally interact only in the presence of the natural activator.

The signal amplification system according to the invention comprises a bacterial multi-hybrid system containing:

(a) a first chimeric polypeptide corresponding to a first fragment of an enzyme;

(b) a second chimeric polypeptide corresponding to a second fragment of an enzyme or a modulating substance capable of activating said enzyme; and (c) a substance capable of stimulating or inhibiting the interaction between a target ligand and a molecule of interest, wherein the first fragment is fused to a molecule of interest and the second fragment or the modulating substance is fused to a target ligand, and wherein the activity of the enzyme is restored by the interaction between the said molecule of interest and the said target ligand, and wherein a signal amplification is generated.

Another aspect of the present invention consists in a method of selecting a molecule of interest, which is capable of binding to target ligand, wherein the interaction between the said molecule of interest and the said target ligand is detected with a signal amplification system according to the invention, by means of signal amplification which triggers transcriptional activation, and is quantified by measuring the synthesis of the signaling molecule or the expression of the reporter gene.

This method of selecting a molecule of interest allows selection of a molecule capable of interacting directly with a predetermined target ligand The signal amplification corresponds to the production of a signaling molecule. This signaling molecule is any molecule capable of leading to a signaling cascade reaction.

In a preferred embodiment of the invention, the signaling molecule corresponds to the synthesis of cAMP.

In another preferred embodiment of the invention, the signaling molecule corresponds to the synthesis of cGMP.

The transcriptional activation leads to a reporter gene, expression of which is selected from the group consisting of gene coding for nutritional marker, such as lactose or maltose; gene conferring resistance to antibiotics such as ampicillin, chloramphenicol, kanamycin, or tetracyclin; a gene encoding for a toxin; a color marker, such as, fluorescent marker of the type of the Green Fluorescent Protein (GFP); a gene encoding phage receptor proteins or a fragment thereof, such as phage 8 receptor, lamb, and any other gene giving a selectable phenotype.

According to a preferred embodiment of the invention, cAMP, upon binding to CAP, is able to activate the transcription of catabolic operons, allowing the bacteria to ferment carbohydrates, such as maltose or lactose, and to express the phage 8 receptor, protein LamB, which could serve as a marker at the bacterial surface. This signal amplification system comprising this bacterial multi-hybrid system is able to reveal, for example, interactions between small peptides (GCN4 leucine zipper), bacterial (tyrosyl tRNA synthetase), or eukaryotic proteins (yeast Prp11/Prp21 complex).

Accordingly, specific reporter cassettes in which any gene of interest is fused to a cAMP/CAP dependent promoter can be designed. Thus, to facilitate the screening and the selection of complex libraries, the construction of such a simple selection system using an antibiotic resistance gene can be performed.

The reporter gene could be a toxin, not naturally present in bacteria, under the control of a cAMP/CAP-dependent promoter. This could be particularly useful to search for chemical compounds or mutations that abolish a given interaction between the target ligand and a molecule of interest. According to this construction, when association between the target ligand and a molecule of interest takes place, cAMP will be produced, the expression of the toxin gene will be switched on, and the cells will be killed. A substance capable of stimulating or inhibiting the interaction between the target ligand and the molecule of interest and that abolishes interaction will shut down toxin gene expression and will enable the cells to grow. An easy selection for substances that abolish interaction between the target ligand and the molecule of interest is resistance to phage 8. The phage receptor, the LamB protein, is the product of the lamB gene, which is part of the maltose regulon, therefore its expression requires cAMP. In consequence, cells producing cAMP will lyse when infected with 8 vir. Substances that abolish interaction between the target ligand and the molecule of interest will abrogate cAMP synthesis and bacteria will become resistant to phage 8. As a result, the cells will grow.

Another selection scheme for compounds or mutations that abolish a given interaction could be designed by constructing a strain that harbors a selectable marker (i.e. a gene conferring resistance to antibiotics such as ampicillin chloramphenicol, kanamycin, tetracyclin, etc.) under the transcriptional control of a promoter that is repressed by cAMP/CAP. Such cAMP/CAP repressed promoter can be engineered by introducing a synthetic CAP binding site within the promotor region as shown by Morita et al. (Morita T, Shigesada K., Kimizuka F., Aiba H. (1988), "Regulatory effect of a synthetic CRP recognition sequence placed downstream of a promoter," Nucleic Acids Res. 16:7315–32).

The International Patent Applications No. WO 96/23898 (Thastrup O. et al.) and No. WO 97/11094 (Thastrup O. et al.), respectively, relating to a method of detecting biologically active substances as Green Fluorescent Protein (GFP), and the International Patent Application No. WO 97/07463 (Chalfie M. et al.) describing the uses of GFP, are herein incorporated by reference, and a novel variant of GFP.

In one specific illustration of the present invention, the method of selecting a molecule of interest consists in a signal amplification system, which comprises a bacterial multi-hybrid system of at least two distinct fragments of an enzyme, whose enzymatic activity is restored by the interaction between the said molecule of interest and the said target ligand. The two fragments are any combination of fragments from the enzyme, which in vitro functionally interact with the natural activator of said enzyme by restoring its activity.

According to the method of selecting a molecule of interest of the present invention, the fragments are selected from the group consisting of:
  (a) a fragment T25 corresponding to amino acids 1 to 224 of CyaA and a fragment T18 corresponding to amino acids 225 to 399 of CyaA;
  (b) a fragment corresponding to amino acids 1 to 224 of CyaA and a fragment corresponding to amino acids 224 to 384 of CyaA;
  (c) a fragment corresponding to amino acids 1 to 137 of CyaA and a fragment corresponding to amino acids 138 to 400 of CyaA;
  (d) a fragment corresponding to amino acids 1 to 317 of CyaA and a fragment corresponding to amino acids 318 to 400 of CyaA; and
  (e) two fragments from eukaryotic adenylate cyclase in association with molecules, such as G protein and forskolin.

And more particularly, the fragments are a fragment T25 corresponding to amino acids 1 to 224 of *Bordetella pertussis* CyaA and a fragment T18 corresponding to amino acids 225 to 399 of *Bordetella pertussis* CyaA.

In another specific illustration of the present invention, the method of selecting a molecule of interest consists in a signal amplification system, which comprises a bacterial multi-hybrid system of at least a first fragment of an enzyme and a modulating substance, whose activity, which is an enzymatic activity, is restored by the interaction between the said molecule of interest and the said target ligand.

In both of the above illustrations of the present invention, the enzyme is selected from the group consisting of adenylate cyclase and guanylate cyclase from any origin, and more preferably the enzyme is the catalytic domain of Bordetella adenylate cyclase (CyaA) located within the first 400 amino acid residues of the adenylate cyclase toxin.

The target ligand according to the invention is selected from the group consisting of protein, peptide, polypeptide, receptor, ligand, antigen, antibody, DNA binding protein, glycoprotein, lipoprotein and recombinant protein.

"Peptide" or "polypeptide" or "protein" refers to a polymer in which the monomers are alpha amino acids joined together through amide bonds. Peptides are two or often more amino acid monomers long. Polypeptides are more then ten amino acid residues. Proteins are more than thirty amino acid residues. Standard abbreviations for animo acids are used herein (see Stryer, 1988, *Biochemistry, Third Ed.*, incorporated herein by reference).

"DNA Binding Protein" refers to a protein that specifically interacts with deoxyribonucleotide strands. A sequence specific DNA binding protein binds to a specific sequence or family of specific sequences showing a high degree of sequence identity with each other (e.g., at least about 80% sequence identity) with at least 100-fold greater affinity than to unrelated sequences. The dissociation constant of a sequence-specific DNA binding protein to its specific sequence(s) is usually less than about 100 nM, and may be as low as 10 nM, 1 nM, 1 pM, or 1 fM. A nonsequence specific DNA binding protein binds to a plurality of unrelated DNA sequences with a dissociation constant that varies by less than 100-fold, usually less than tenfold, to the different sequences. The dissociation constant of a nonsequence specific DNA binding protein to the plurality of sequences is usually less than about 1:m. In the present invention, DNA binding protein can also refer to an RNA binding protein.

"Recombinant protein" refers to a protein made up of at least two separate amino acid chains, which are naturally not contiguous. For example, any fusion protein like Lac repressor-β-galactosidase, any protein or polypeptide like the tyrosyl-tRNA synthetase like leucine zipper derived from protein GCN4.

According to the method of selecting a molecule of interest of the present invention, the molecule of interest is capable of interacting with the target ligand and possibly of binding to said target ligand.

In a specific embodiment of the method of selecting a molecule of interest of the present invention, the molecule of interest is a mutant molecule compared to the known wild type molecule, and said molecule of interest is tested for its capacity of interacting with the target ligand.

The present invention further relates to a kit for selecting a molecule of interest, wherein said kit comprises:
  (a) a signal amplification system according to the invention;
  (b) an *E. coli* strain, or any bacterial strain deficient in endogenous adenylate cyclase, or any other eukaryotic cell; and
  (c) a medium allowing the detection of the complementation selected from the group consisting of indicator plate or selective medium as minimal medium supplemented with lactose or maltose as unique carbon source, or medium with antibiotics, or medium to visualize fluorescence, conventional medium, and medium which allows sorting by the presence of the phage receptor. The indicator plate is, for example, a MacConkey agar medium supplemented with lactose or maltose.

A bacterial strain deficient in endogenous adenylate cyclase means that this strain is not capable of cAMP synthesis.

The present invention also relates to a kit for selecting a molecule of interest, wherein said kit comprises:
  (a) a signal amplification system according to the invention, wherein the molecule of interest is a mutant molecule compared to the known wild type molecule;
  (b) a signal amplification system according to the invention, wherein the molecule of interest is the known wild type molecule as the control;
  (c) *E. coli* strain, or any bacterial strain deficient in endogenous adenylate cyclase or any other eukaryotic cell; and
  (d) a medium allowing the detection of complementation selected from the group consisting of indicator or selective medium as minimal medium supplemented with lactose or maltose as unique carbon source, medium with antibiotics, medium to visualize fluorescence, conventional medium and medium which allows the sorting by the presence of the phage receptor for each signal amplification system; and
  (e) means for detecting whether the signal amplification system with the mutant molecule is enhanced or inhibited with respect to the signal amplification system with wild type molecule.

The present invention includes a molecule of interest identified by the method of selecting a molecule of interest according to the present invention.

The present invention further includes a molecule of interest corresponding to a polynucleotide capable of expressing a molecule, which interacts with a fused target ligand coupled with an enzyme or a fragment thereof.

According to another aspect, the invention also concerns a method of screening for a substance capable of stimulating or inhibiting the interaction between a target ligand and a molecule of interest, wherein the stimulating or the inhibiting activity is detected with a signal amplification system according to the invention, by means of generating a signal amplification and triggering transcriptional activation, and wherein said signal amplification and said triggering transcriptional activation are compared with those obtained from an identical signal amplification system without any substance.

The method of screening for substance capable of stimulating or inhibiting the interaction between a target ligand and a molecule of interest allows the choice of a substance acting positively or negatively or even not acting in this interaction.

In the method of screening for a substance capable of stimulating the interaction between a target ligand and a molecule of interest according to the invention, the signal amplification corresponds to the production of a signaling molecule and the transcriptional activation leads to a reporter gene expression.

In the method of screening for substance capable of inhibiting the interaction between a target ligand and a molecule of interest according to the invention, the signal amplification corresponding to the production of a signaling molecule is blocked or partially abolished and the transcriptional activation leading to a reporter gene expression is also blocked or partially abolished.

In one specific illustration of the present invention, the method of screening for a substance capable of stimulating or inhibiting the interaction between a target ligand and a molecule of interest, consists in a signal amplification system, which comprises a bacterial multi-hybrid system of at least two distinct fragments of an enzyme, whose enzymatic activity is restored by the interaction between the said molecule of interest and the said target ligand. The two fragments are any combination of fragments from the enzyme, which in vitro functionally interact with the natural activator of said enzyme by restoring its activity.

According to the method of screening for substance capable of stimulating or inhibiting the interaction between a target ligand and a molecule of interest of the present invention, the fragments are selected from the group consisting of:

(a) a fragment T25 corresponding to amino acids 1 to 224 of CyaA and a fragment T18 corresponding to amino acids 225 to 399 of CyaA;

(b) a fragment corresponding to amino acids 1 to 224 of CyaA and a fragment corresponding to amino acids 224 to 384 of CyaA;

(c) a fragment corresponding to amino acids 1 to 137 of CyaA and a fragment corresponding to amino acids 138 to 400 of CyaA;

(d) a fragment corresponding to amino acids 1 to 317 of CyaA and a fragment corresponding to amino acids 318 to 400 of CyaA; and (e) two fragments from eukaryotic adenylate cyclase in association with molecules, such as G protein, and forskolin.

And more particularly, the fragments are a fragment T25 corresponding to amino acids 1 to 224 of *Bordetella pertussis* CyaA and a fragment T18 corresponding to amino acids 225 to 399 of *Bordetella pertussis* CyaA.

In another specific illustration of the present invention, the method of screening for a substance capable of stimulating or inhibiting the interaction between a target ligand and a molecule of interest, consists in a signal amplification system, which comprises a bacterial multi-hybrid system of at least a first fragment of an enzyme and a modulating substance, whose activity, which is an enzymatic activity, is restored by the interaction between the said molecule of interest and the said target ligand.

In both of the above illustrations of the present invention, the enzyme is selected from the group consisting of adenylate cyclase and guanylate cyclase from any origin, and more preferably the enzyme is the catalytic domain of Bordetella adenylate cyclase (CyaA) located within the first 400 amino acid residues of the adenylate cyclase toxin.

The present invention further relates to a method of screening for a substance capable of stimulating or inhibiting the interaction between a target ligand and a molecule of interest, wherein the substance is selected from the group consisting of protein, glycoprotein, lipoprotein, ligand, and any other drug having stimulating or inhibitory affinity.

The present invention also provides a kit for screening for a substance capable of stimulating or inhibiting the interaction between a target ligand and a molecule of interest, wherein said kit comprises:

(a) a signal amplification system according to the invention with the substance capable of stimulating or inhibiting the interaction between a target ligand and a molecule of interest;

(b) a signal amplification system according to the invention without any substance as the control;

(c) *E. coli* strain, or in any bacterial strain deficient in endogenous adenylate cyclase, or any other eukaryotic cell; and (d) a medium allowing for the detection of the complementation selected from the group consisting of indicator plate or selective medium as minimal medium supplemented with lactose or maltose as unique carbon source, medium with antibiotics, medium to visualize fluorescence, conventional medium, and medium that allows the sorting by the presence of the phage receptor; and (e) means for detecting whether the signal amplification system with the substance is enhanced or inhibited with respect to the signal amplification system without any substance.

The present invention includes a substance capable of stimulating or inhibiting the interaction between a target ligand and a molecule of interest identified by the method of screening for a substance capable of stimulating or inhibiting the interaction between a target ligand and a molecule of interest according to the present invention.

According to a preferred embodiment of the invention, the selection and the screening are performed in an *E. coli* strain, or in any bacterial strain deficient in endogenous adenylate cyclase, or any other eukaryotic cell.

Functional analysis of *B. pertussis* adenylate cyclase activity can be easily monitored in an *E. coli* strain deficient in endogenous adenylate cyclase. In *E. coli,* cAMP bound to the transcriptional activator, CAP (catabolite activator protein), is a pleiotropic regulator of the expression of various genes, including genes involved in the catabolism of carbohydrates, such as lactose or maltose (Ullmann, A. & Danchin, A. (1983) in *Advances in Cyclic Nucleotide Research* (Raven Press, New York), Vol. vol. 15, pp. 1–53). Hence, *E. coli* strains lacking cAMP are unable to ferment lactose or maltose. When the entire catalytic domain of CyaA (amino acids 1 to 399) is expressed in *E. coli* cya under the transcriptional and translational control of lacZ (plasmid pDIA5240), its calmodulin-independent residual activity is sufficient to complement an adenylate cyclase deficient strain and to restore its ability to ferment lactose or maltose (Ladant, D., Glaser, P. & Ullmann, A. (1992) *J. Biol. Chem.* 267, 2244–2250). This can be scored either on indicator plates (i.e. LB-X-Gal or MacConkey media supplemented with maltose) or on selective media (minimal media supplemented with lactose or maltose as unique carbon source).

The fact that the genetic tests according to the invention are carried out in *E. coli* greatly facilitates the screening as well as the characterization of the interaction between the target ligand and the molecule of interest. Firstly, it is possible to use the same plasmid constructs to screen a library to identify the molecule of interest, also called a putative binding partner, to the target ligand, also called a given "bait", and then to express the target ligand and the molecule of interest in order to characterize their interaction by in vitro binding assays.

Secondly, the high efficiency of transformation that can be achieved in *E. coli*, allows the analysis of libraries of high complexity. This is particularly useful for i) the screening and the selection of peptides from a library made from random DNA sequences that present an affinity for a given bait protein, and ii) the exhaustive analysis of the network of interactions between the proteins of a given organism (Bartel, P. L., Roecklein, J. A., SenGupta, D. & Fields, S. (1996) *Nature Genetics* 12, 72–7; Fromont, R. M., Rain, J. C. & Legrain, P. (1997) *Nature Genetics* 16, 277–82).

The present invention further relates to a polynucleotide sequence coding for a signal amplification system according to the invention, wherein the polynucleotide sequence codes for a bacterial multi-hybrid system of at least two chimeric polypeptides containing:

(a) a first chimeric polypeptide corresponding to a first fragment of an enzyme fused to a molecule of interest; and (b) a second chimeric polypeptide corresponding to a second fragment of an enzyme or a modulating substance capable of activating said enzyme fused to a target ligand.

The present invention also relates to a polynucleotide sequence coding for the signal amplification system according to the invention, wherein the polynucleotide sequence codes for a bacterial multi-hybrid system containing:

(a) a first chimeric polypeptide corresponding to a first fragment of an enzyme fused to a molecule of interest;

(b) a second chimeric polypeptide corresponding to a second fragment of an enzyme or a modulating substance capable of activating said enzyme fused to a target ligand; and (c) a substance capable of stimulating or inhibiting the interaction between a target ligand and a molecule of interest.

This invention will be described in greater detail with reference to the following examples.

EXAMPLE 1

DHP1 is an adenylate cyclase deficient (cya) derivative of DH1 (F-, glnV44 (AS), recA1, endA1, gyrA96 (Nal'), thi1, hsdR17, spoT1, rfbD1) (25), and was isolated using phosphomycin as a selection antibiotic (Alper, M. D. & Ames, B. N. (1978) *J. Bacteriol.* 133, 149–57). Growth media used were the rich medium LB or the synthetic medium M63 (Miller, J. H. (1972) *Experiments in molecular genetics* (Cold Spring Harbor Laboratory, Cold Spring Harbor, N.Y.)) supplemented with 1% carbon source. Antibiotic concentrations were as follows: ampicillin 100 mg/ml and chloramphenicol 30 mg/ml. Screening for the ability to ferment sugars was performed either on MacConkey agar plates containing 1% maltose, or on LB plates containing 40 mg/ml X-Gal (5-Bromo-4-chloro-3-indolyl-b-D-galactopyranoside) and 0.5 mM IPTG (Isopropyl-b-D-thiogalactopyranoside).

EXAMPLE 2

Plasmid pKT25 (3445-bp) is a derivative of the low copy vector pSU40 (expressing a kanamycin resistance selectable marker) that encodes the T25 fragment. It was constructed as follows: a 1044-bp HindIII-EcoRI, fragment of pT25 was first subcloned into pSU40 linearized with HindIII and EcoRI, resulting in pKT25L. pKT25 was generated from pKT25L by deleting a 236-bp NheI-HindIII fragment.

Plasmid pUT18 (3023-bp) is a derivative of the high copy number vector pUC19 (expressing an ampicillin resistance selectable marker and compatible with pT25 or pKT25) that encodes the T18 fragment (amino acids 225 to 399 of CyaA). In a first step, we constructed plasmid pUC19L by inserting a 23 bp double-stranded oligonucleotide (5'-AATTCATCGATATAACTAAGTAA-3') and its complementary sequence) between the EcoRI and NdeI sites of pUC19. Then, a 534-bp fragment harboring the T18 open reading frame was amplified by PCR (using appropriate primers and pT18 as target DNA) and cloned into pUC19L digested by EcoRI and ClaI (the appropriate restriction sites were included into the PCR primers). In the resulting plasmid, pUT18, the T18 open reading frame is fused in frame downstream of the multicloning site of pUC19. This plasmid is designed to create chimeric proteins in which a heterologous polypeptide is fused to the N-terminal end of T18 (see map).

Plasmid pUT18C (3017-bp) is a derivative of pUC19 (expressing a ampicillin resistance selectable marker and compatible with pT25 or pKT25) that encodes the T18 fragment. It was constructed by subcloning the same 534-bp PCR-amplified fragment harboring the T18 open reading frame described above into pUC19L linearized by HindIII and PstI (the appropriate restriction sites were included into the PCR primers). In the resulting plasmid, pUT18C, the T18 open reading frame is fused in frame upstream of the multicloning site of pUC19L. This plasmid is designed to create chimeric proteins in which a heterologous polypeptide is fused to the C-terminal end of T18 (see map).

Plasmid pKT25-zip (3556-bp) is a derivative of pKT25 that was constructed by inserting a DNA fragment (PCR-amplified using appropriate primers) encoding the leucine zipper region of GCN4 into pKT25 cleaved by KpnI, as described above.

Plasmid pUT18-zip (3125-bp) is a derivative of pUT18 that was constructed by inserting a 114bp DNA fragment (PCR-amplified using appropriate primers) encoding the leucine zipper region of GCN4 into pUT18 linearized by KpnI and EcoRI Plasmid pUT18C-zip (3119-bp) is a derivative of pUT18C that was constructed by inserting the same 114-bp DNA fragment encoding the GCN4 leucine zipper described above into pUT18 linearized by KpnI and EcoRI

EXAMPLE 3

Briefly, a cAMP-biotinylated-BSA conjugate was coated on ELISA plates and non-specific protein binding sites were blocked with BSA. Boiled bacterial cultures were then added, followed by diluted rabbit anti-cAMP antiserum in 50 mM Hepes pH 7.5, 150 mM NaCl, 0.1% Tween 20 (HBST buffer) containing 10 mg/ml BSA. After overnight incubation at 4° C., the plates were washed extensively with HBST, then goat anti-rabbit IgG coupled to alkaline phosphatase (AP) was added and incubated for 1 hr at 30° C. After washing, the AP activity was revealed by 5'-paranitrophenyl phosphate. cAMP concentrations were calculated from a standard curve established with known concentrations of cAMP diluted in LB medium.

EXAMPLE 4

Two compatible plasmids (derived from pACYC184 and pBluescript-II-KS) that express either the T25 fragment corresponding to amino acids 1 to 224 of CyaA or the T18 fragment corresponding to amino acids 225 to 399 were constructed. A multicloning site was fused to the C-terminal end of T25 to facilitate construction of fusions with foreign proteins. Similarly, the T18 fragment was fused in frame to alacZ of pBluescript-II-KS downstream of its multicloning siteK (FIG. 2).

The two plasmids, pT25 and pT18, were co-transformed in DHP1, a cya derivative of the *E. coli* strain DH1 (Hanahan, D. (1983) *J. Mol. Biol.* 166, 557–80), and plated on MacConkey agar supplemented with maltose. As expected, no spontaneous complementation between the two isolated (independently expressed) fragments could be detected in vivo: all the transformants were white (see Table 1). When the DHP1 strain was transformed with a plasmid expressing the full catalytic domain, all colonies were red (Table 1).

To test whether functional complementation between T25 and T18 could be brought about by fusing them to interacting proteins, there was inserted, within the multicloning site of both pT25 and pT18, a DNA sequence that codes for a 35 amino acid long leucine zipper derived from protein GCN4, a yeast transcriptional activator (Blondel, A. & Bedouelle, H. (1991) *Protein Engineering* 4, 457–61). When the resulting plasmids, pT25-zip and pT18-zip, were co-transformed in DHP1 and plated on MacConkey/maltose media, the resulting colonies became red after 24–30 hours of growth at 30° C. (Table 1).

Control experiments were carried out in which pT25-zip was co-transformed with pT18, or pT18-zip was co-transformed with pT25. None of the transformants exhibited complementation, demonstrating that the functional complementation of T25-zip and T18-zip was mediated by the interaction of their leucine zipper motif. The efficiency of complementation could be further quantified by measuring in liquid cultures, either cAMP levels or β-galactosidase activities (Table 1).

Adenylate cyclase activities of the different transformants were measured in cell extracts in the presence of CaM that binds tightly to T25 and T18 fragments to form the active adenylate cyclase complex. As shown in Table 1, only the extract from DHP1/pT25-zip/pT18-zip exhibited a significant enzymatic activity. The lack of activity in the extracts of the three other types of transformants indicates that, at least one of the two complementary fragments of adenylate cyclase was missing, most probably as a consequence of its in vivo proteolytic degradation. Therefore, it would appear that the association of T25-zip and T18-zip, through their leucine zipper motif, not only resulted in their functional complementation, but also in their stabilization. Stabilization of protein fragments (a and w peptides) through complementation (Ullmann, A., Jacob, F. & Monod, J. (1968) *J. Mol. Biol.* 32, 1–13) has also been observed for β-galactosidase.

TABLE 1

Analysis of complementation in DHP1 strain

| Plasmids | Phenotype on Mac Conkey/ maltose | β-galac- tosi- dase[a] | cAMP[b] | Adenylate cyclase activity[c] + CaM | − CaM |
|---|---|---|---|---|---|
| none | White | 179 | <10 | <1 | <0.01 |
| pCm-AHL1 | Red/24 hrs | 6650 | 3400 | 13,000 | 10 |
| pT25 + pTi8 | White/72 hrs | 130 | <10 | <1 | <0.01 |
| pT25 + pTi8-zip | White/72 hrs | 183 | <10 | <1 | <0.01 |
| pT25-zip + pT18 | White/72 hrs | 178 | <10 | <1 | <0.01 |
| pT25-zip + pT18-zip | Red/30 hrs | 4750 | 1100 | 10,000 | 4 |

[a]units/mg dry weight bacteria
[b]pmol/mg dry weight bacteria
[c]nmol CAMP protein; when present in the assays, CaM was at a concentration of 1 micromolar. Bacteria were grown in LB at 30° C. in the presence of 0.5 mM IPTG plus appropriate antibiotics. The results represent the average values obtained for at least five independent cultures, which differed by less than 10%.

EXAMPLE 5

Screening for in vivo protein-protein interactions by using functional complementation of T25 and T18 was carried out.

The goal was to examine whether the complementation between T25 and T18 could be used to analyze interactions between proteins larger than the 35-residue long leucine zipper motif. A DNA fragment that encodes the N-terminal part (residues 1 to 290) of the dimeric tyrosyl tRNA synthetase from *Bacillus stearothermophilus* (Guez-Ivanier, V. & Bedouelle, H. (1996) *J. Mol. Biol.* 255, 110–120) was subdoned into the multicloning site of plasmids pT25 and pT18. The resulting plasmids, pT25-TyrRS and pT18-TyrRS, when co-transformed in DHP1, yielded red transformants on MacConkey/maltose. The transformants synthesized cAMP and expressed β-galactosidase (Table 2). Control transformations confirmed that the TyrRS moiety was responsible for the functional complementation between T25-TyrRS and T18-TyrRS. Furthermore, no complementation occurred when T25-TyrRS was cotransformed with pT18-zip or vice versa. This demonstrates that the complementation was dictated by the specificity of recognition of the polypeptides fused to the two fragments, T25 and T18.

It was further shown (Table 2) that the bacterial multi-hybrid system could detect interaction between the yeast splicing factors Prp11 and Prp21 (fused to T25 and T18, respectively) that was previously characterized in the yeast two-hybrid assay (Legrain, P. & Chapon, C. (1993) *Science* 262, 108–10). This demonstrates that this bacterial complementation assay can reveal association between eukaryotic proteins.

TABLE 2

Complementation between various chimeric proteins

| Plasmids | Phenotype on Mac Conkey/ maltose | β-galac- tosi- dase[a] | CAMP[b] |
|---|---|---|---|
| pT25-Tyr + pT18-Tyr | Red/40 hrs | 2800 | 580 580 |
| pT25-Tyr + pT18 | White/96 hrs | 193 | <10 10 |
| pT25 + pT18-Tyr | White/96 hrs | 183 | <10 <0.01 |

TABLE 2-continued

Complementation between various chimeric proteins

| Plasmids | Phenotype on Mac Conkey/ maltose | β-galac- tosi- dase[a] | CAMP[b] |
|---|---|---|---|
| pT25 – Tyr + PT18-zip | White/96 hrs | 134 | <10 | <0.01 |
| pT25-zip + pT18 – Tyr | White/96 hrs | 126 | <10 | <0.01 |
| pT25-prp11 + pT18-prp21 | Red/40 hrs | 850 | 65 | 4 |

[a]units/mg dry weight bacteria
[b]pmol/mg dry weight bacteria
Bacteria were grown in LB at 30° C. in the presence of 0.5 mM IPTG plus appropriate antibiotics. The results represent the average values obtained for at least five independent cultures.

To mimic a screening procedure, plasmids pT18-zip and pT18-TyrRS were mixed with about a 5-fold excess of pT18 and co-transformed this mixture in DHP1 with either pT25 or pT25-zip. The transformants were plated on LB-X-Gal. All the colonies co-transformed with pT25 were white (FIG. 3). Around 20% of the colonies were blue when the cells were co-transformed with the mixture of pT18 derivatives and pT25-zip. The plasmid DNAs of these clones were further analyzed by restriction mapping. As expected, the blue colonies among the bacteria co-transformed with pT25-zip harbored only pT18-zip.

In another series of experiments, pT18-zip was mixed with a 1,000 fold excess of pT18 and this mixture was transformed in DHP1 harboring pT25-zip and plated on MacConkey/maltose. Three red colonies were identified among about 3,000 white ones. Plasmid DNA analysis of the Mal+clones confirmed the presence of pT18-zip. Transformation of the same mixture of pT18-zip/pT18 into DHP1 harboring pT25 gave no Mal+ clones out of 10,000 analyzed (data not shown). These results indicate that the functional complementation between the adenylate cyclase fragments could be used to identify interacting proteins in *E. coli*.

Finally, an examination was made to determine whether the complementation between T25 and T18 could be used in a selection procedure rather than using the screening described above. DHPI bacteria cotransformed with complementing plasmids (pT25-zip/pTI8-zip or pT25-TyrRS/pT18-TyrRS) were able to grow on minimal media supplemented with lactose or maltose as unique carbon sources, while bacteria cotransformed with non-complementing plasmids (pT25-zip/pTI8-TyrRS or pT25-TyrRS/pT18-zip) did not grow.

To determine whether this selection could be used to identify interacting proteins among an excess of non-interacting ones, the following "model screening" was performed on selective media: DHP1 bacteria harboring pT25-zip and pT18-zip (expected phenotype: Lac+) were mixed with a $10^5$-excess of DHP1/pT25/pT18 (expected phenotype: Lac), and then $10^7$ cells from this mixture were plated on minimal media supplemented with lactose plus antibiotics. After 4–5 days at 30° C., 100 to 200 Lac+ colonies appeared. Plasmid DNA analysis indicated that 18 out of 20 of these colonies tested harbored pT25-zip and pT18-zip. When $10^7$ DHP1/pT25/pT18 cells were plated on minimal media/lactose, about 10 colonies were detected: these cells appeared to represent spontaneous revertants of DHP1 to a Lac+ phenotype (due to either reversion of cya− to cya+ or to cAMP/CAP independent lac promoter mutations). This "model screening" demonstrates that bacteria expressing specific interacting proteins fused to the adenylate cyclase fragments could be selected among a large number (here a $10^5$-fold excess) of irrelevant clones.

EXAMPLE 6

A further test was carried out to determine whether functional complementation could be obtained when the interacting polypeptide is fused at the C-terminus of T18 rather than at its N-terminus. Two new plasmids derived from the pUC19 vector were constructed for this purpose. In pUT18, the T18 polypeptide is fused in frame downstream to the multicloning site of pUC19, whereas in pUT18C, the T18 polypeptide is fused in frame upstream of the multi-cloning site. A DNA fragment encoding the leucine zipper of GCN4 was then cloned in frame into both pUT18 and pUT18C to yield pUT18-zip and pUT18C-zip.

As shown in Table 3, cotransformation of DHP1 with pT25-zip and either pUT18-zip or pUT18C-zip led to functional complementation. This indicates that interacting polypeptides could be fused at both ends of the T18 fragment with the same complementation efficiency. Similar results were obtained (Table 3) when the T25-zip chimeric protein was expressed from a pSU40 derivative that expresses the kanamycin resistance selectable marker (pKT25-zip).

TABLE 3

Comparison of complementation between N-terminal and C-terminal fusion proteins

| Plasmids | Phenotype on MacConkey/maltose | β-galactosidase units/mg dry weight bacteria |
|---|---|---|
| pT25 + pT18 | White/ 72 hrs | 154 |
| pT25-zip + pUT18-zip | Red/ 26 hrs | 5100 |
| pT25-zip + pUT18 | White/ 72 hrs | ND |
| pT25 + pUT18-zip | White/ 72 hrs | ND |
| pT25-zip + pUT18-zip | Red/ 26 hrs | 6180 |
| pT25-zip + pUT18C | White/ 72 hrs | ND |
| pT25 + pUT18C-zip | White/ 72 hrs | ND |
| pT25-zip + pUT18C-zip | Red/ 26 hrs | 6100 |
| pKT25-zip + pUT18 | White/ 72 hrs | ND |
| pKT25 + pUT18-zip | White/ 72 hrs | ND |
| pKT25-zip + pUT18-zip | Red/ 26 hrs | ND |
| pKT25-zip + pUT18C | White/ 72 hrs | ND |
| pKT25 + pUT18C-zip | White/ 72 hrs | ND |
| pKT25-zip + pUT18C-zip | Red/ 26 hrs | ND |

Bacteria were grown in LB at 30° C. in the presence of appropriate antibiotics.
ND: not done.

EXAMPLE 7

The bacterial two-hybrid system was used to analyze interactions between various sub-domains of the dimeric tyrosyl-tRNA synthetase from *B. stearothennophilus*, (TyrPS), which is a symmetrical dimer (Brick, P. and D. M. Blow (1987) *J Mol. Biol.* 194,2 87–297). Its monomer is composed of two domains. Deletion of the C-terminal domain (321–419) of TyrRS produces a truncated ΔTyrRS which activates tyrosine as the full-length molecule but is no longer able to bind the cognate tRNA. The truncated AtyrRS (1–320) forms a dimer that closely resembles the wild-type one.

The crystal structure of the dimeric ΔTyrRS revealed that each monomer contains two structural domains: an α/β domain (1–220) containing six-stranded β-sheets and an α-helical domain (221–320) containing five helices (Brick, P. and D. M. Blow 1987) *J. Mol. Biol.* 194,287–297). The dimer is formed by the association of a hydrophobic surface encompassing residues 128–167 within the α/β domain of each subunit.

To analyze interactions between various sub-domains, different fragments of the TyrRS polypeptide (generated by PCR using appropriate primers) were fused in frame with either the T25 or the T18 fragment and the resulting chimeric proteins were tested for functional complementation in DPH1. The results, summarized in FIG. 5, revealed 3 different types of interactions between the TyrRS monomers or between the TyrRS sub-domains:

1) Dimerisation through the α/β domains as can be seen in the crystal structure of TyrRS. For instance, the chimeric protein T18-TyrRS1-249, which harbors only the α/β domain, can fully complement T25-TyrRS1-333, which contains both the α/β and a domains. Previous studies have shown that introduction of charged residues into the hydrophobic subunit interface of dimeric TyrRS induces reversible dissociation (Ward, W. H. J., H. Jones, and A. R. Ferscht (1987) *Biochemistry* 26, 4131–4138) Confirmation that a point mutation that converts Phe164 to Arg abolishes the interaction between the α/β domains (as shown by the absence of functional complementation) has been made.

2) Dimerisation through the α domains, which has not been previously predicted from the crystal structure of TyrRS. Analysis of complementation between various fragments indicated that this dimerisation is mediated by the C-terminal region of the (α domain (FIG. 5)). This region contains a pseudo leucine zipper motif (LLL on FIG. 5) made of 3 leucine residues at positions 298, 305, and 312. The same segment can also mediate a specific interaction with the GCN4 leucine-zipper (FIG. 5).

3) Interaction between the α/β domain and the a domain.

This study illustrates the interest of the bacterial two-hybrid in delineating interacting domains of proteins and shows that it could reveal interactions, which occur in vivo and that were not expected from the three dimensional structure.

EXAMPLE 8

The two-hybrid system was also used to analyze the dimerization of a DNA-binding protein from *B.pertussis*, BvgA. BvgA is a transcriptional regulator, which in *B.pertussis* controls the expression of virulence-associated genes. It is a member of the bacterial two-component signal transduction family, together with its cognate sensor protein, BvgS (Scarlato et al. (1990) *Proc. Nad. Acad. Sci. USA*, 87:6753). The transmembrane BvgS is autophosphorylated in response to environnemental signals and subsequently phosphorylates BvgA. BvgA, in its phosphorylated form, can bind to specific DNA sequences within the promoter of several virulence genes and activates their transcription. Several studies previously suggested that BvgA might have the capacity to dimerize although a direct demonstration that BvgA is a dimer is still lacking.

To study the dimerization of BvgA, a set of plasmids was constructed that encode various fragments of the BvgA polypeptide fused to either T25 or T18. These plasmids were co-transformed in DHP1 (FIG. 6), and the level of functional complementation between the different chimeric proteins was determined by measuring β-galactosidase activities. These results indicate that BvgA can indeed dimerize and that the critical region required for dimerization is localized within the central part of the protein.

EXAMPLE 9

A selection procedure was also established that will permit an easy screening for mutations that abolish the interaction between two hybrid proteins. This selection is based on the well established fact that *E.coli* cya$^+$ strains are resistant to phage λ, whereas *E.coli* cya strains are sensitive. The phage receptor, the LamB protein, is the product of the lamB gene, which is part of the maltose regulon; therefore, its expression requires cAMP. In consequence, cells producing cAMP will lyse when infected with λ.vir. Molecules or mutations that abolish the interaction between two hybrid proteins will abrogate cAMP synthesis, and, therefore, the cells should become resistant to phage λ.

Quantification of resistance to phage λ.vir has been performed in liquid Luria broth. Experimental conditions of infection that enable complete lysis of cAMP producing bacteria are the following:

multiplicity of infection: 2 to 10, $MgSO_4$ concentration: 20 mM, incubation time at 37° C. under aeration for 2 to 3 hours.

DHP1 bacteria were grown overnight in the presence of 1 mM cAMP in Luria broth. The bacteria were washed 3 times with Luria broth, and an aliquot was immediately infected with λ.vir. Another aliquot was diluted and cultivated in the absence of cAMP at 37° C. After 15 generations of growth, a sample of the bacteria grown in the absence of cAMP has been infected with λ.vir. After serial dilutions, bacteria were plated on solid Luria broth and counted. Out of $1.6 \times 10^8$ bacteria grown in the absence of cAMP $1.2 \times 10^8$ phage resistant clones were counted (75%), whereas out of $1.3 \times 10^8$ bacteria grown in the presence of cAMP, only 140 λ-resistant clones (frequency of $10^{-6}$) were found. These latter λ-resistant clones were white on MacConkey maltose plates, suggesting that they were cAMP-independent malT mutants.

Plasmids useful for practicing this invention have been deposited at Collection Nationale de Cultures de Microorganismes in Paris, France on Nov. 25, 1998, as follows:

| Plasmid | Accession No. |
| --- | --- |
| XL-1/pUT18 | I-2092 |
| XL-1/pUT18C | I-2093 |
| XL-1/pT25 | I-2094 |
| XL-1/pKT25 | I-2095 |

As it appears from the teachings of the specification, the invention is not limited in scope to one or several of the above detailed embodiments; the present invention also embraces all the alternatives that can be performed by one skilled in the same technical field, without deviating from the subject or from the scope of the instant invention.

What is claimed is:

1. A bacterial multi-hybrid signal amplification system comprising:
(a) a first chimeric polypeptide comprising a first fragment of an enzyme chosen from adenylate cyclase and guanylate cyclase;
(b) a second chimeric polypeptide comprising a second fragment of an enzyme chosen from adenylate cyclase and guanylate cyclase, or a modulating substance capable of activating adenylate cyclase or guanylate cyclase, and
(c) a signal molecule precursor,
wherein the first fragment is fused to a molecule of interest, and the second fragment or the modulating substance is fused to a target ligand, and wherein the activity of the enzyme is restored by the in vivo interaction between the molecule of interest and the target ligand and wherein a signal molecule is generated by the restored enzyme activity; and
wherein the in vivo interaction occurs in a bacterial cell.

2. The bacterial multi-hybrid signal amplification system of claim 1, wherein the enzyme is a bacterial enzyme.

3. The bacterial multi-hybrid signal amplification system according to claim 2, wherein the enzyme is the catalytic domain of Bordetella adenylate cyclase.

4. The bacterial multi-hybrid signal amplification system according to claim 3, wherein the first and the second fragments are any combination of fragments of the same enzyme.

5. The bacterial multi-hybrid signal amplification system according to claim 4, wherein the first and the second fragments are selected from the group consisting of:
(a) a fragment corresponding to amino acids 1 to 224 of adenylate cyclase and a fragment corresponding to amino acids 225 to 399 of adenylate cyclase;
(b) a fragment corresponding to amino acids 1 to 224 of adenylate cyclase and a fragment corresponding to amino acids 225 to 384 of adenylate cyclase;
(c) a fragment corresponding to amino acids 1 to 137 of adenylate cyclase and a fragment corresponding to amino acids 138 to 400 of adenylate cyclase;
(d) a fragment corresponding to amino acids 1 to 317 of adenylate cyclase and a fragment corresponding to amino acids 318 to 400 of adenylate cyclase; and
(e) two fragments from eukaryotic adenylate cyclase.

6. The bacterial multi-hybrid signal amplification system according to claim 4 or 5, wherein the first fragment is a fragment corresponding to amino acids 1 to 224 of *Bordetella pertussis* adenylate cyclase and the second fragment is a fragment corresponding to amino acids 225 to 399 of *Bordetella pertussis* adenylate cyclase.

7. The bacterial multi-hybrid signal amplification system according to any one of the claims 1 or 3, wherein the modulating substance is a natural activator of the enzyme, or a fragment of said natural activator.

8. The bacterial multi-hybrid signal amplification system according to claim 7, wherein the natural activator is calmodulin, or a fragment thereof, and said first fragment is mutated compared to the wild type enzyme.

9. The bacterial multi-hybrid signal amplification system according to claim 8, wherein the first fragment is a mutated fragment of the catalytic domain of Bordetella adenylate cyclase.

10. The bacterial multi-hybrid signal amplification system of claim 3, wherein the catalytic domain comprises the first 400 amino acid residues of the adenylate cyclase.

11. A kit for selecting a molecule of interest, said kit comprising:
(a) a bacterial multi-hybrid signal amplification system according to claim 1;
(b) a bacterial strain or eukaryotic cell line deficient in endogenous adenylate cyclase; and
(c) a medium allowing the detection of the interaction selected from the group consisting of i) indicator or selective medium as minimal medium supplemented with lactose or maltose as a unique carbon source, ii) medium with antibiotics, iii, medium to visualize fluorescence, iv) conventional medium, and v) medium which allows the sorting by the presence of the phage receptor.

12. The kit for selecting a molecule of interest according to claim 11, wherein the bacterial strain is an *E. coli* strain.

13. A kit for selecting a molecule of interest, said kit comprising:
   (a) a bacterial multi-hybrid signal amplification system according to claim 1, wherein the molecule of interest is a mutant molecule compared to a known wild type molecule;
   (b) a bacterial multi-hybrid signal amplification system according to claim 1, wherein the molecule of interest is a known wild type molecule as a control;
   (c) a bacterial strain or eukaryotic cell line deficient in endogenous adenylate cyclase;
   (d) a medium allowing the detection of the interaction selected from the group consisting of i) indicator or selective medium as minimal medium supplemented with lactose or maltose as a unique carbon source, ii) medium with antibiotics, iii) medium to visualize fluorescence, iv) conventional medium, and v) medium which allows the sorting by the presence of the phage receptor; and
   (e) means for detecting whether the signal amplification system with the mutant molecule is enhanced or inhibited with respect to the signal amplification system with wild type.

14. The kit for selecting a molecule of interest according to claim 13, wherein the bacterial strain is an *E. coli* strain.

15. A kit for screening for a substance capable of stimulating or inhibiting the interaction between a target ligand and a molecule of interest, said kit comprising:
   (a) a bacterial multi-hybrid signal amplification system according to claim 1 with the substance capable of stimulating or inhibiting the interaction between a target ligand and a molecule of interest;
   (b) a bacterial multi-hybrid signal amplification system according to claim 1 without any substance as the control;
   (c) a bacterial strain or eukaryotic cell line deficient in endogenous adenylate cyclase; and
   (d) a medium allowing the detection of the interaction selected from the group consisting of i) indicator plate or selective medium as minimal medium supplemented with lactose or maltose as a unique carbon source, ii) medium with antibiotics, iii) medium to visualize fluorescence, iv) conventional medium, and v) medium which allows the sorting by the presence of the phage receptor; and
   (e) means for detecting whether the signal amplification system with the substance is enhanced or inhibited with respect to the signal amplification system without any substance.

16. The kit for selecting a molecule of interest according to claim 15, wherein the bacterial strain is an *E. coli* strain.

17. The bacterial multi-hybrid signal amplification system according to claim 1, further comprising:
   a substance capable of stimulating or inhibiting the interaction between a target ligand and a molecule of interest.

18. The kit for selecting a molecule of interest according to claim 16, wherein the bacterial strain is an *E. coli* strain.

19. The bacterial multi-hybrid signal amplification system according to claim 1, wherein the first fragment comprises the catalytic domain of Bordetella adenylate cyclase.

20. The bacterial multi-hybrid signal amplification system according to claim 19, wherein the second chimeric polypeptide comprises a modulating substance capable of activating adenylate cyclase.

21. The bacterial multi-hybrid signal amplification system according to claim 20, wherein the modulating substance is calmodulin.

* * * * *